United States Patent [19]

Stein et al.

[11] Patent Number: 5,240,163
[45] Date of Patent: Aug. 31, 1993

[54] LINEAR SURGICAL STAPLING INSTRUMENT

[75] Inventors: Jeffrey A. Stein, Milford, Conn.; David Schiff, Philadelphia, Pa.; Paul Mulhauser, New York; Donald Lamond, Long Beach, both of N.Y.

[73] Assignee: American Cyanamid Company, Stamford, Conn.

[21] Appl. No.: 785,290

[22] Filed: Oct. 30, 1991

[51] Int. Cl.[5] ............................................ A61B 17/072
[52] U.S. Cl. ...................................... 227/175; 227/19
[58] Field of Search .................. 227/19, 178, 180, 175

[56] References Cited
U.S. PATENT DOCUMENTS

| 3,675,688 | 7/1972 | Bryan et al. | 227/19 X |
| 5,018,657 | 5/1991 | Pedlick et al. | 227/19 X |
| 5,040,715 | 8/1991 | Green et al. | 227/180 X |
| 5,084,057 | 1/1992 | Green et al. | 227/19 X |

Primary Examiner—Frank T. Yost
Assistant Examiner—Rinaldi Rada
Attorney, Agent, or Firm—Ronald A. Clayton; Charles F. Costello, Jr.

[57] ABSTRACT

A surgical stapling instrument includes a staple cartridge that may be loaded with surgical staples, an anvil mounted to confront the staple cartridge for deforming staples driven theretoward, and advancer for advancing the staple cartridge from an open position toward the anvil to a closed position for clamping tissue to be sutured therebetween, and a driver for driving the staples from the cartridge toward the anvil through tissue clamped between the cartridge and the anvil. A trigger for operating the driver, and a safety mechanism linked to the advancer preventing the trigger from operating the driver when the cartridge is in the open position but permits the trigger to operate the driver only when the cartridge is in the closed position. In addition, a coupling mechanism can removably mount a head assembly and a handle assembly, with each assembly containing a portion of the advancer and driver. The coupling mechanism can also include a rotatable mechanism for permitting relative rotation between the handle assembly and the head assembly. The advancer includes a clamp lever that articulates first in the forward direction and then in a downward direction. The staple cartridge can include a housing loaded with at least one staple and a comb with at least one tooth. The comb is driven by the driver to drive the staple and can be of varying lengths to compliment the staple.

16 Claims, 15 Drawing Sheets

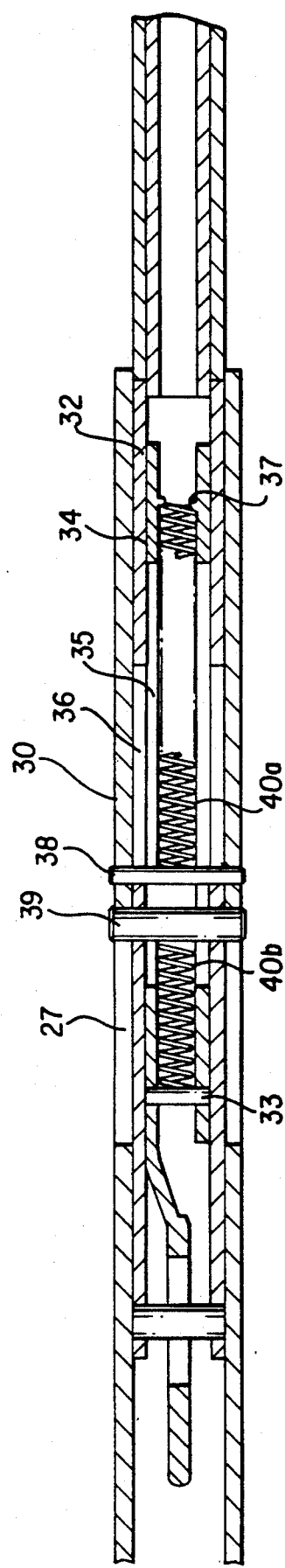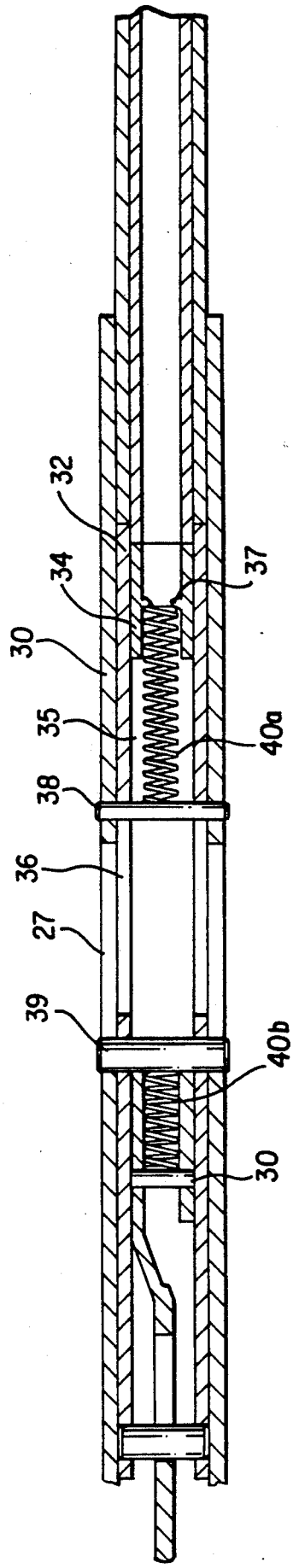

LINEAR SURGICAL STAPLING INSTRUMENT

BACKGROUND OF THE INVENTION

1. Field of the Invention

The present invention relates to a linear anatomic surgical stapling instrument and a surgical staple magazine used therein. More particularly, the invention relates to a transverse anatomic stapling instrument, which is also known as a transverse anastomosis instrument or device, for suturing body organs and tissue.

2. Description of the Prior Art

Historically, suturing of a surgical or other wound in organs and tissue has been done by hand. Conventional hand suturing techniques require a high degree of surgical skill. However, expertise in such techniques can vary widely from surgeon to surgeon, thereby resulting in widely varying quality in performance of the concluding steps of an operative procedure. In addition, even very skillful surgeons require a considerable amount of time to suture even relatively small wounds. Therefore, it is possible that an undesirable amount of blood may be lost during the suturing operation.

Accordingly, there has been an increasing tendency in recent years to use surgical staples to suture body organs and tissue after a medical procedure. Surgical staples have been particularly effective in suturing body organs and tissue such as the lung, as well as the esophagus, the stomach, the duodenum, and other body organs in the intestinal tract.

The advent of surgical stapling has provided several marked advantages over known hand suturing techniques. First, since one or more rows of surgical staples are inserted into tissue using a specially adapted instrument that is relatively simple to operate, near uniformity of the closure from one surgeon to the next results. In addition, all staples in the closure are usually inserted simultaneously or in rapid sequence across the entire wound. Therefore, the closure is made very quickly to minimize loss of blood.

The specially adapted instruments for inserting surgical staples are mechanically operated and may be known as anastomosis devices, such as the transverse anastomosis devices of the type to which this invention relates. In such devices, the staples are loaded in one or more elongated rows into a magazine or cartridge. The magazine is then mounted in the device, which includes a mechanism for pushing, or driving, the staples from the magazine through two or more sections of tissue toward a deforming anvil. At the conclusion of the driving operation, the legs of each staple are clamped or bent, by engagement with the anvil, to a closed configuration to complete the suture and join the tissue sections together.

Known surgical stapling instruments of the type described above can be made of reusable materials. However, most stapling instruments employed today are made of disposable materials so that they can be discarded after use on a single patient. The cost of manufacture is thereby lowered and problems associated with handling, repairing, reconditioning, and sterilizing of previously used instruments are eliminated. Specifically, the risk of spreading infection from patient to patient due to improperly sterilized instruments is thus reduced and the surgeon can be confident that each fresh instrument he or she picks up is in good working order.

The conventional surgical anastomosis stapling instruments, of the type to which the present invention relates, more particularly include a handle having a trigger for firing the instrument and an elongated neck extending to a U-shaped distal end. A pair of jaws, one supporting an anvil and the other adapted to receive a disposable staple cartridge or magazine are mounted at the distal end to define the U-shape, which extends transversely to the neck. A clamp is provided to close the space between the anvil and the staple cartridge on the tissue layers to be sutured. Squeezing the trigger then drives the rows of staples, usually simultaneously, through the tissue layers and against the anvil where they are deformed to complete the suture.

While such known stapling instruments provide the advantage of surgical stapling mentioned above, they are nevertheless characterized by certain drawbacks. For example, these instruments are conventionally made of one-piece construction, with the distal end for receiving the staple cartridge extending from the handle. The design, however, can only be used with surgical staple magazines of one length. If a shorter or longer staple magazine is better suited for a particular suturing procedure, that is, to make a shorter or longer closure, a different size stapling instrument must be used. A second drawback of conventional one-piece stapling instruments is that the distal end resides in a fixed position with respect to the handle. Therefore, manipulation of the instrument to properly align the staple magazine and anvil carried in the distal end with the tissue to be sutured may be difficult because the entire stapling instrument must be maneuvered.

Still another drawback of known stapling instruments is that if the trigger is accidentally squeezed a staple cartridge will be wasted. More importantly, time will be wasted while the spent staple cartridge is replaced with a loaded cartridge and undesirable blood loss in the interim may result. While it is known to provide a safety latch on stapling instruments of the type described above to lock the trigger, the operator must remember to set the safety latch before and after the instrument is used for the latch to be effective.

Still, another difficulty with known stapling instruments is in obtaining proper alignment between and subsequent uniform clamping of the staple cartridge and the anvil together to clamp tissue therebetween. Proper alignment of the staple cartridge with the anvil is necessary to ensure the staples are properly deformed when driven toward the anvil, and uniform clamping of the tissue is desirable to properly position the tissue for suturing. In known instruments, however, the staple cartridge is pivoted about a supporting axis toward the anvil at one end of both to squeeze the tissue. However, this arrangement produces a non-uniform clamping force against the tissue because a greater force tends to be applied to the tissue closer to the pivot point.

Accordingly, further advantages and improvements in linear surgical stapling instruments are needed.

SUMMARY OF THE INVENTION

Accordingly, it is a principle object of the present invention to improve upon and enhance the benefits obtained by using linear surgical stapling instruments.

It is an object of the present invention to provide a surgical stapling instrument having an automatically engaged safety mechanism that prevents accidental unwanted firing of the instrument.

It is a further object of the invention to provide a linear surgical stapling instrument having improved mechanisms for swiftly and accurately aligning a magazine carrying surgical staples and an anvil for deforming the staples to ready the instrument for use.

It is still a further object of the invention to provide a two-part transverse anastomosis-type linear surgical stapling instrument that can be used with interchangeable head assemblies having staple magazines of differing lengths, thereby to offer greater surgical flexibility.

It is still a further object of the invention to provide a linear surgical stapling instrument with a clamp lever that moves along a path of natural thumb movement of the operator.

It is still a further object of the invention to provide a staple cartridge for a surgical stapling instrument which can be used with surgical staples of different lengths.

These and other objects are achieved by the surgical stapling instrument of the present invention, which in a preferred embodiment comprises a staple cartridge that may be loaded with surgical staples, an anvil mounted to confront the staple cartridge for deforming staples driven theretoward, an advancer for advancing the staple cartridge from an open position toward the anvil to a closed position for clamping tissue to be sutured therebetween, and a driver for driving the staples from the cartridge toward the anvil through tissue clamped between the cartridge and the anvil. A trigger operates the driver, and a safety mechanism linked to the advancer prevents the trigger from operating the driver when the cartridge is in the open position but permits the trigger to operate the driver only when the cartridge is in the closed position.

A surgical stapling instrument in accordance with the present invention thus provides a safety mechanism which only permits the trigger to operate the driver when the cartridge is in the closed position.

In accordance with another aspect of the present invention, the preferred embodiment is a surgical stapling instrument comprising a head assembly including a staple cartridge that may be loaded with surgical staples, an anvil mounted to confront the staple cartridge for deforming staples driven theretoward, a primary advancer operable to advance the staple cartridge from an open position toward the anvil to a closed position for clamping tissue to be sutured therebetween, and a primary driver operable to drive the staples from the cartridge through tissue toward the anvil to deform the staples. In addition, a handle assembly includes a second advancer couplable with the primary advancer to operate the primary advancer, and a secondary driver couplable with the primary driver to operate the primary driver. A coupling mechanism removably mounts the handle assembly and the head assembly together, with the secondary advancer coupled to the primary advancer and with the secondary driver coupled to the primary driver.

Accordingly, the present invention also provides a coupling mechanism for mounting the handle assembly and the head assembly together. In this manner, a two-piece surgical stapling instrument with a head assembly removable from a handle assembly for replacement by a different head assembly is provided.

In accordance with still another aspect of the subject invention, a preferred embodiment is a surgical stapling instrument comprising a head assembly including a staple cartridge that may be loaded with surgical staples, an anvil mounted to confront the staple cartridge for deforming staples driven theretoward, a primary advancer operable to advance the staple cartridge from an open position toward the anvil to a closed position for clamping tissue to be sutured therebetween, and a primary driver operable to drive staples from the cartridge through tissue toward the anvil to deform the staples. A handle assembly includes a secondary advancer couplable with the primary advancer to operate the primary advancer, and a secondary driver couplable with the primary driver to operate the primary driver. A coupling assembly mounts the handle assembly and the head assembly together along a longitudinal axis, and provides a rotatable mechanism for permitting the head assembly to rotate relative to the handle assembly about a longitudinal axis.

Thus, the present invention provides a rotating mechanism for permitting relative rotation between the head assembly and the handle assembly so that the head assembly can be placed in any desired rotary position relative to the handle assembly.

In accordance with yet another aspect of the subject invention, a preferred embodiment is a surgical stapling instrument comprising a housing, a staple cartridge mountable with the housing that may be loaded with surgical staples, an anvil mounted with the housing to confront the staple cartridge for deforming staples driven theretoward and an advancer mounted in the housing for reciprocal movement along a longitudinal axis to advance the staple cartridge from an open position toward the anvil to a closed position for clamping tissue to be sutured therebetween. A driver drives the staples from the cartridge toward the anvil through tissue clamped between the cartridge and the anvil, and a trigger operates the driver. An articulated clamp lever is linked near one end of the advancer, and a crank is linked to the clamp lever near an end thereof opposite to the one end and to the housing, with the crank mounting the clamp lever to advance the advancer first by movement of the opposite end generally parallel to the longitudinal axis and thereafter by movement of the opposite end toward the longitudinal axis.

Accordingly, the present invention also provides a clamp lever that articulates first forwardly and then downwardly with a natural thumb movement of the operator.

In accordance with still another aspect, in a preferred embodiment the present invention is a surgical stapling instrument having a staple cartridge that may be loaded with surgical staples and an anvil mounted to confront the cartridge to deform staples driven theretoward. An advancer advances the cartridge from an open position toward the anvil to a closed position for clamping tissue to be sutured therebetween. A driver is arranged to drive staples from the cartridge toward the anvil through tissue between the cartridge and anvil. A trigger actuates the driver and includes a cam surface engageable with a cam follower when the trigger is operated to actuate said driver to an extreme position and thereafter provide tactile feedback when that extreme position has been reached.

In accordance with still another aspect of the subject invention, a preferred embodiment of a cartridge for a surgical stapling instrument mountable to confront a staple deforming anvil, comprises a housing having at least one guideway for receiving a surgical staple therein. The guideway has a fixed length and is aligned with the anvil for directing the staple theretoward when the cartridge and the anvil are mounted to confront each other. A comb having at least one tooth is also received in the guideway, with the length of the tooth and the length of the staple received in the guideway collectably substantially equalling the length of the guideway. Therefore, the cartridge can be configured to drive staples of different lengths by varying the length of the tooth.

Thus, the present invention provides a staple cartridge wherein staples of different lengths can be used simply by varying the length of the staple driving tooth.

These and other objects, aspects, features, and advantages of the present invention will become apparent from the following detailed description of the preferred embodiment taken in conjunction with the drawings.

BRIEF DESCRIPTION OF THE DRAWINGS

FIGS. 2A and 2B are partial horizontal cross-sectional views of the head assembly shown respectively in the open and clamped positions;

DESCRIPTION OF THE PREFERRED EMBODIMENT

Figure 1:
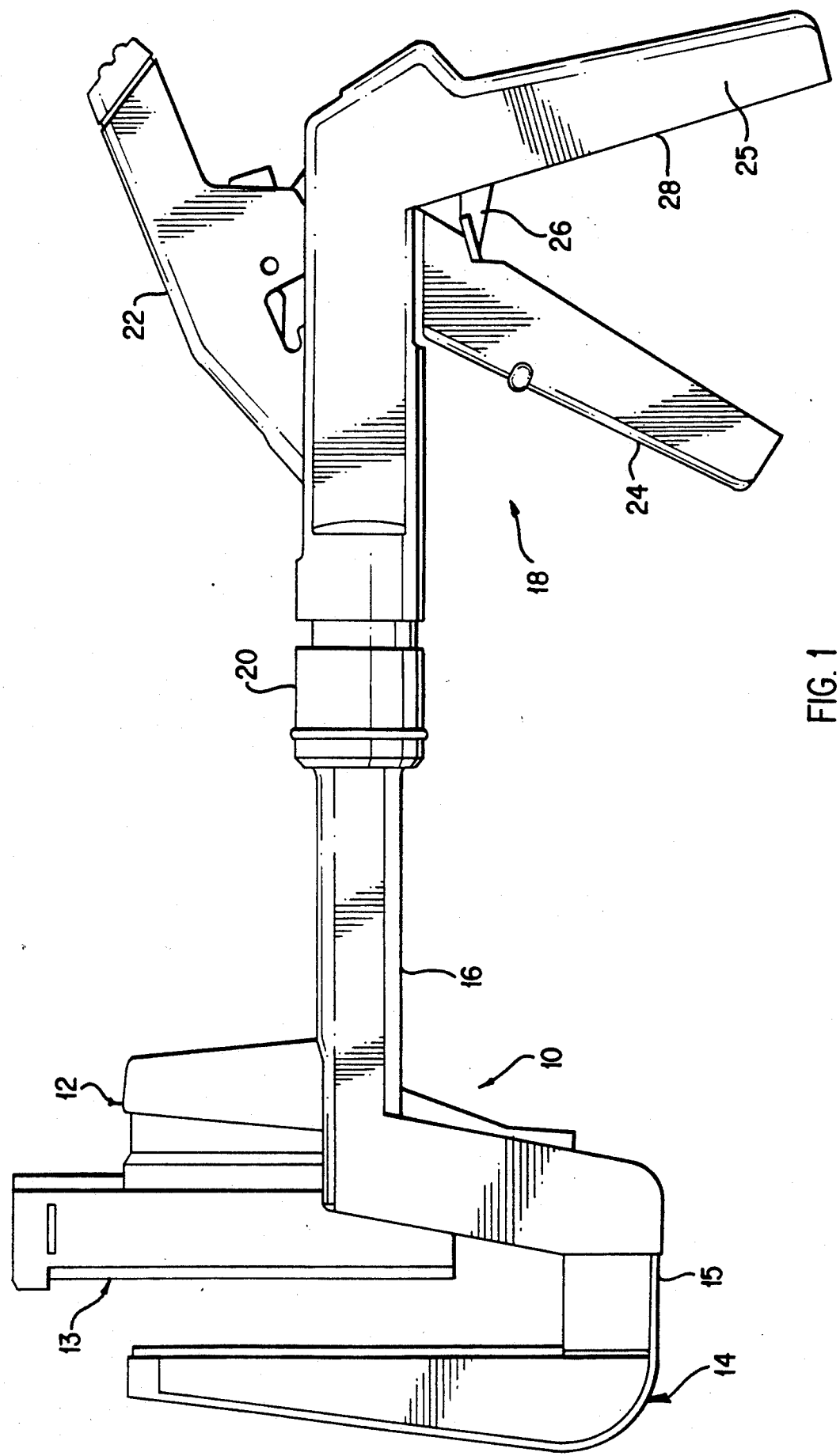
FIG. 1 is a side elevational view of a linear surgical stapling instrument in accordance with a preferred embodiment of the present invention.

FIG. 1 illustrates the two major components comprising the transverse anastomosis surgical stapling instrument in accordance with the preferred embodiment of the present invention. Generally speaking, these components include a head assembly 10 having a first staple cartridge receiving jaw 12 and a second staple deforming jaw 14 connected to each other by a bridge 15 to define a U-shape in elevation. A staple cartridge 13 may be slidably inserted into the staple cartridge receiving jaw 12. A head housing 16 contains the inner working components of the head assembly 10 which will be discussed in detail below.

The head assembly 10 is detachably connected to a handle assembly 18 by means of a bayonet collar 20.

The handle assembly includes a handle housing 28 on which a clamp lever 22 is pivotably mounted. When actuated the clamp lever advances the staple cartridge receiving jaw 12 toward the staple deforming jaw 14 to clamp tissue between the jaws. A trigger 24 is also pivotably mounted in the housing 28 and when squeezed relative to a complementary grip 25 actuates a driving mechanism, not shown in FIG. 1, to drive the staples from the cartridge 13 through tissue clamped between the jaws. A safety latch 26 carried in the housing 28 prevents premature squeezing of the trigger 24.

FIGS. 2, 2A, 2B and 3 will now be used to provide a detailed explanation of the elements comprising the head assembly 10. Initially referring to FIG. 3, it will be seen that the head comprises two complementary halves 16a and 16b in which a head frame 30, also comprising complementary halves 30a and 30b, is coaxially disposed. (For convenience, in FIGS. 2, 6, and 8 through 13 the head halves 16a and 16b and head frame halves 30a and 30b are shown as a unitary structure, and may be referred collectively as the "head frame.") A staple cartridge advancer 32 and a staple driver 34 are carried for axial reciprocal movement in the head frame 30, which is mounted in a stationary position within the head housing 16. The driver 34 is formed with a driver slot 35 and the advancer 32 is formed with a similar but offset advancer slot 36. A pin 38 fixed in the inside of the head frame 30 extends through the slots 35 and 36. A first driver spring 40a is compressed between the pin 38 and punched nubs 37 inside a rear portion of the driver 34 to bias the driver 34 in a rearward direction. A larger frame pin 39 is fixed in the advancer 32 forwardly of the pin 38 and is received in an enlarged portion of the driver slot 35 and in a housing slot 27 formed in the head frame 30. Finally another pin 33 is fixed within a forward portion of the driver 34 and a second driver spring 40b compressed between the pins 39 and 33 urges the driver 34 forwardly relative to the advancer 32. Thus as will be understood from FIGS. 2 and 2A, in the open rest position the driver 34 is urged rearwardly by the spring 40a, pulling the advancer 32 rearwardly through interaction of the pin 33, the spring 40b, and the frame pin 39, until the frame pin 39 engages the rear extreme of the housing slot 27 and the pin 38 is engaged by the forward extreme 31 of the advancer slot 36.

When the advancer 32 is moved forwardly as described in detail below, the frame pin 39 is moved until it engages the forward extreme of housing slot 27 and the driver 34 is carried forwardly with it by interaction of the pin 32 and spring 40b with the pin 39, as shown in FIG. 2B. A degree of lost motion is permitted between the advancer 32 and driver 34 by the spring 40b as shown by comparison of FIGS. 2A and 2B.

Figure 2:
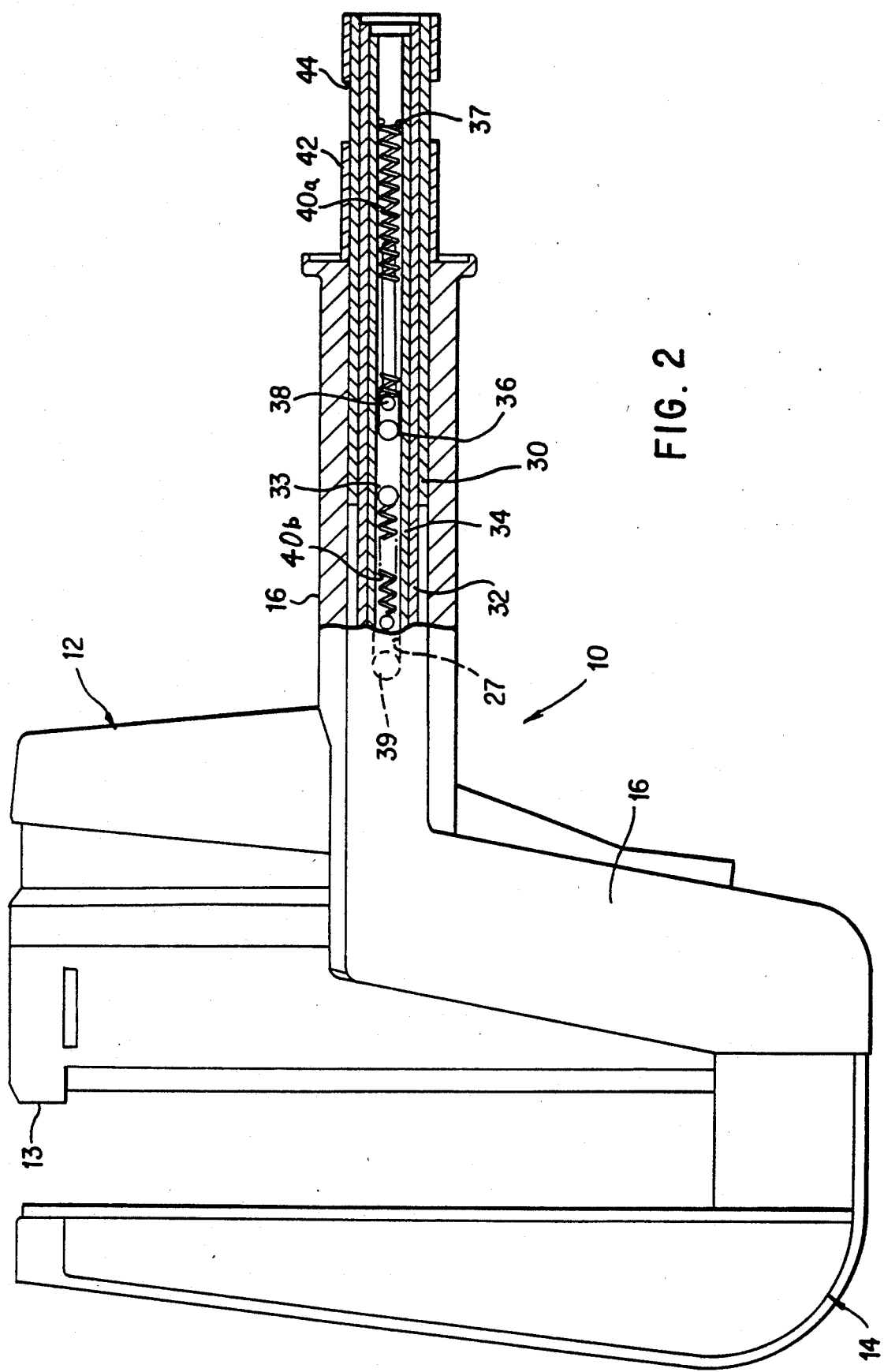
FIG. 2 is a partial vertical cross-sectional view of a head assembly of the surgical stapling instrument in accordance with the preferred embodiment of the present invention.

As depicted in FIG. 2, a female bayonet engagement ring 42 may be fit on the rear end of the head frame 30. The engagement ring is cylindrical in shape and defines an annular groove 44 about its circumference. If desired the ring 42 can be made of two pieces mounted on the rear end of the head frame and separated to define the groove.

Referring again to FIG. 3, it can be seen that the advancer 32 has a forked end 46 which is connected to a carrier lever 50. The driver 34 has a shaft 51, a transverse driving blade 58 carried at the distal end of the shaft, and a slot 60 formed in the blade 58. The shaft 51 of the driver 34 slides coaxially within the advancer 32, with the shaft 51 and the forked end 46 extending in opposite directions through a back opening 52 in the carrier lever 50. These three elements are connected together by a pin 56 extending through holes 48 in the forked end 46, the slot 60 in the driving blade 58, and holes 54 in the carrier lever 50. A carrier housing 62, having a rear insertion slot 61 that fits within the carrier lever 50, supports a carrier track 70 in its front end.

Both the carrier housing 62 and the carrier track 70 have open backs through which the driving blade 58 may advance. A carrier pin 66 is received loosely in a hole 64 in the top of the carrier housing and the head of the pin abuts the inside confronting surface of the carrier lever 50 above a ridge 63. A compression carrier spring 68 encircling the carrier pin 66 biases the top of carrier lever 50 rearwardly as a pivot end 53 of the carrier lever pivots about the bottom of the carrier housing 62. The carrier track 70 is formed with elongated rails 72 for receiving complementary channels, not shown, in a cartridge housing 76 loaded with staples, thereby to mount the cartridge with the carrier housing. The carrier track 70 also includes a stepped pivot arm 74 that functions in a manner to be discussed below.

The cartridge housing 76 preferably includes two rows of guideways 79, each guideway being loaded with a surgical staple 78. The cartridge housing also carries a staple driving comb 80 behind the staples. The present invention contemplates using combs with teeth 81 of different lengths such that the combined length of a staple and the length of a comb tooth substantially equal the length of each guideway. Thus, using combs with different length teeth allows staples of various lengths to be fired without changing the clamping stroke or firing stroke of the stapling instrument.

The cartridge housing 76 can be loaded with conventional surgical staples made of an inert metal like stainless steel or titanium, or alternatively, bioabsorbable or partially bioabsorbable polymeric staples, for example, as described in copending U.S. patent applications Ser. Nos. 07/548,802, and 07/548,803, both filed Jul. 6, 1990, which are incorporated herein by reference. The bioabsorbable or partially bioabsorbable surgical staples are malleable like stainless steel staples, and thus can bent into complex shapes that are then retained. The only adjustment that may be made to the stapling instrument of the present invention when using the polymeric staples as described above is to use an anvil made of plastic and specifically designed for use with polymeric staples.

A cartridge pin 82 extends through a compression cartridge spring 84 and fits loosely through an opening 86 in the top of the cartridge housing.

The staple deforming jaw 14 includes an L-shaped anvil shroud 88, a similarly shaped anvil rail 90 and an anvil 92. All three pieces are connected to a U-shaped extension 94 of the head frame 30, comprising the bridge 15, by means of rivets 96, 98, 100, and 102. The carrier track 70 is attached to the anvil rail 90 by means of a pin 104, which extends through holes 106 in the pivot arm 74 and a slot 108 in the anvil rail 90. In this way, the carrier housing 62 is guided to slide back and forth by engagement of the pin 104 in the slot 108 in a direction perpendicular to a longitudinal axis of the stapling instrument. This guided movement causes an even, uniform force to be applied to tissue clamped between the cartridge 76 and the anvil 92 when the two are urged together as described in greater detail below.

Figure 4:
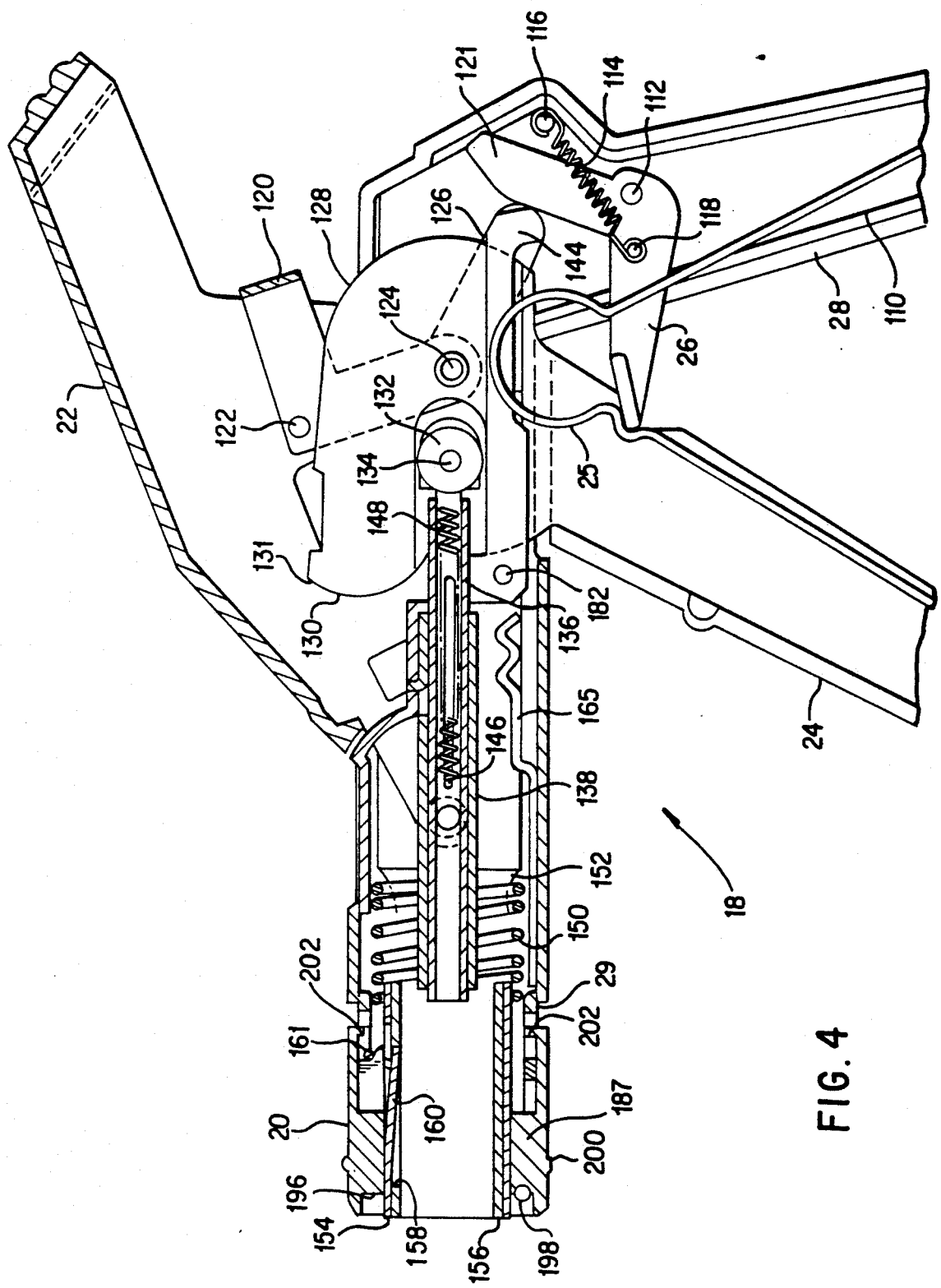
FIG. 4 is a vertical cross-sectional view of a handle assembly of the surgical stapling instrument in accordance with the preferred embodiment of the present invention.
Figure 5:
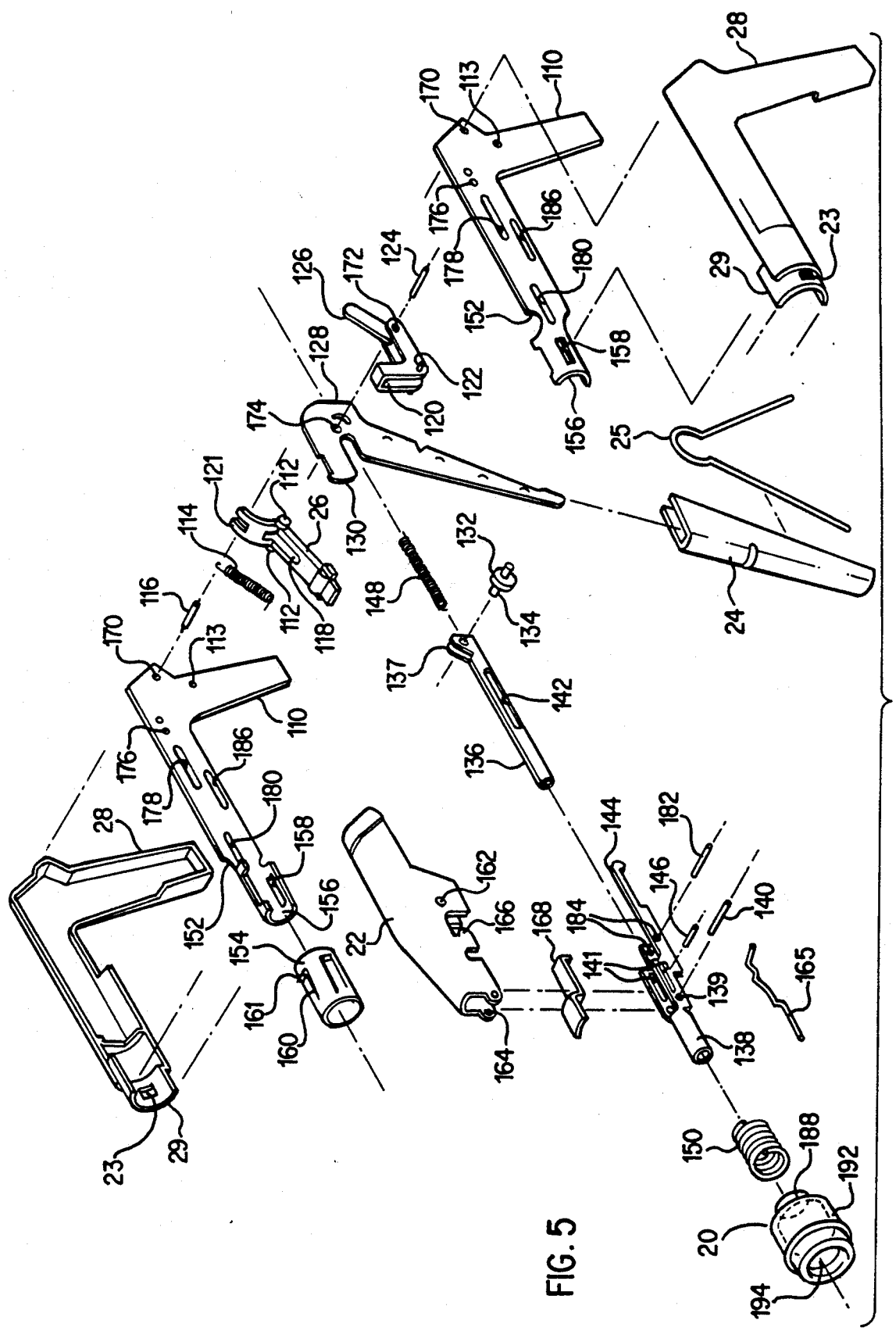
FIG. 5 is an exploded perspective view of the handle assembly shown in FIG. 4.

The handle assembly 18 of the surgical stapling instrument of the present invention will now be described with reference to the vertical cross-sectional view of FIG. 4 and the exploded perspective view of FIG. 5. First referring to FIG. 5, it can be seen that a two complementary part handle frame 110 is disposed within the handle housing 28, which also has two complementary parts. The safety latch 26 is pivotably mounted with the handle frame 110 by pin extensions 112 received in mating holes 113 in the opposing frame parts. A safety tension spring 114 is connected between rivet 116 mounted in the handle frame 110 and spring rod 118 in the safety latch 26. The safety spring 114 biases the safety latch in either the engaged or actuated position, shown in FIG. 4, or in the nonengaged or released position, shown in FIGS. 11 and 12, since the axis along which it is in tension may lie on either side of the axis of pin extensions 112. An L-shaped safety crank 120 is pivotably attached to the clamp lever 22 and to the handle frame 110 to be articulated therebetween. Specifically, the safety crank 120 fits inside a downwardly facing channel formed in the clamp lever 22, with pivot pins 122 received through holes 162 in the clamp lever, and a rivet 124 extending through a hole 172 in the safety crank 120 and mounted in fixed position in the handle frame 110 at intermediate holes 176, as shown in FIG. 5. The L-shaped safety crank 120 has link 126 that engages a follower 121 on the safety latch 26 when the clamp lever is open to lock the safety latch in the actuated position as shown in FIG. 4. The crank is rotated in a counter-clockwise direction when the clamp lever is closed to permit the safety latch to be disengaged from the trigger in a manner described later herein.

FIGS. 4 an 5 also show a trigger cam 128 housed within the trigger 24. A trigger spring 25 has one leg received in the trigger 24 and other leg retained in the handle frame 110 to urge the trigger to the open position shown in FIG. 4. The trigger cam 128 features a rounded cam surface 130 for engaging a roller bearing 132 when the trigger 24 is squeezed. The roller bearing 132 is connected by a bearing pin 134 to a winged tail section 137 of secondary driver 136. The secondary driver 136 is slidably coaxially disposed within a secondary advancer 138.

The clamp lever 22 is connected to the secondary advancer 138 and the secondary driver 136 by a connecting pin 140 which extends through holes 139, shown only in FIG. 5, in the secondary advancer 138 and a secondary driver slot 142 in the secondary driver 136. A pin 146 extends through the slot 142 in the secondary driver 136 and a secondary advancer slot 141 in the secondary advancer 138 and is fixed with the handle frame 110. The fixed pin 146 is connected to a compression secondary driver spring 148, which is tacked to a rear portion of the secondary driver 136 to bias the secondary driver 136 and the secondary advancer 138 in the rearward direction. The secondary advancer 138 includes a stepped extension 144 which moves rearwardly and pushes the safety latch 26 to an actuated position when the clamp lever 22 is moved to the open position. A detent spring 165 is secured to the handle housing 28 and engages a detent pin 182 in the secondary advancer 138 when the clamp lever is actuated.

A collar spring 150 fits over a tapered portion 152 of the handle frame 110. At the distal end of the handle assembly, a collet 154 fits over the nose 156 of the handle frame 110, and the bayonet collar 20 fits over the collet. Elongated slots 158 in the nose 156 of the handle frame align with cut-out flexible fingers 160 in the collet 154. The flexible fingers 160 each include an upstanding tab 161 for actuating the flexible fingers.

FIG. 5 also shows additional details of the clamp lever 22 that were suggested above. Particularly, the clamp lever includes holes 162 for receiving the pin 122 of safety link 120 and holes 164 for receiving connecting pin 140 as discussed above. A notch 166 in the clamp lever receives the bearing pin 134 when the trigger 24 is squeezed as also will be discussed in more detail below. A lockout indicator 168 fits between the clamp lever 22 and the secondary advancer 138. When the clamp lever 22 is properly closed, the lockout indicator 168 indicates that the stapling instrument is ready to fire.

FIG. 5 also shows how the right and left handle frames 110 are joined. Beginning from the proximal portion of the handle frame, a rivet 116, which supports safety spring 114, extends through rear holes 170 in the handle frame 110. A stepped rivet 124 extends through a link hole 172 in the crank 120 and trigger cam hole 174 in the trigger cam 128 and is received on either end by an intermediate hole 176 in each of the parts of the handle frame 110. First upper slots 178 receive the ends of the bearing pin 134 and second upper slots 180 receive the ends of the connecting pin 140 to guide sliding movement of the bearing 132 to the secondary driver 136 and the secondary advancer 138 with the handle frame 110. Finally, the detent pin 182 extends through guide holes 184 in the secondary advancer 138 and through lower slots 186 in the handle frame 110.

Figure 6:
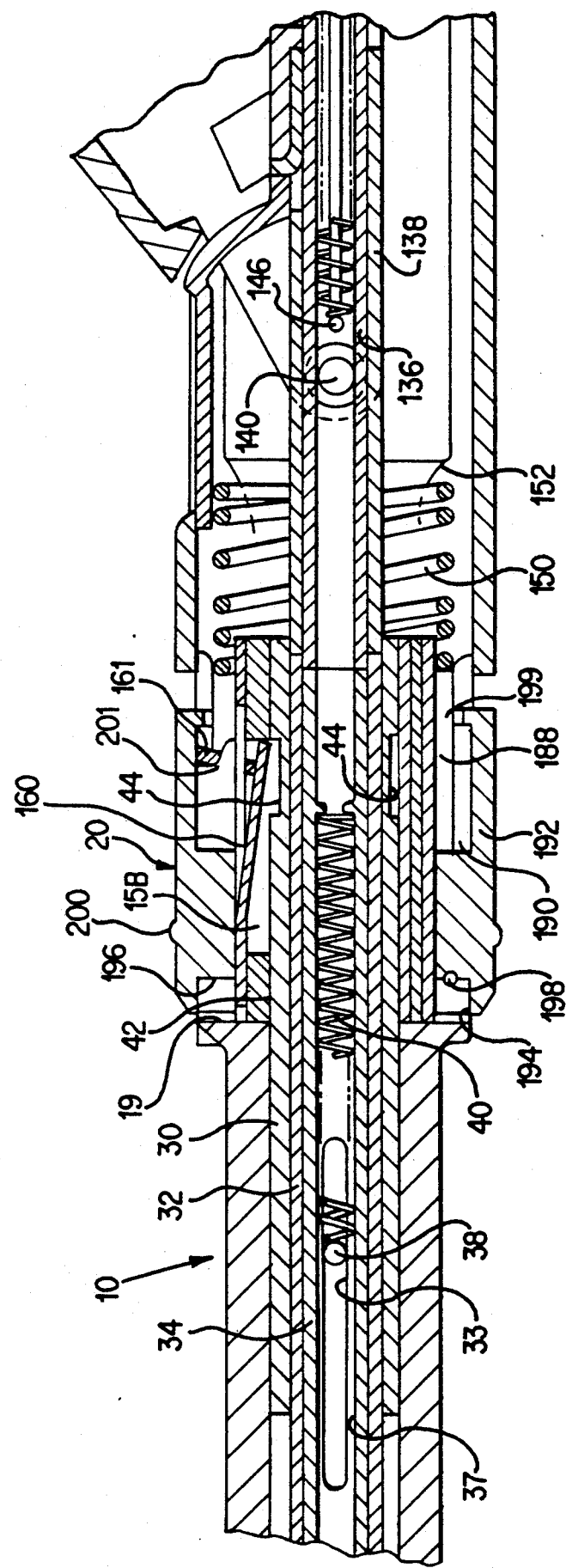
FIG. 6 is an enlarged vertical cross-sectional view of a section of the stapling instrument in accordance with the present invention where the head and handle assemblies are connected together.

Details of the bayonet collar 20 are shown in FIGS. 4 and 6. More specifically, the collar 20 has a double cylinder configuration at one end, with an inner cylinder 188 and an outer cylinder 192 defining an annular opening 190 therebetween. The other end of the bayonet collar has a stepped opening 194 for receiving engagement ring 42 and other portions of the rearward end of the head assembly 10. The stepped opening is defined by an annular detent surface 196 having radially spaced raised spherical detents 198. The outer surface of the collar has an annular ridge 200 for ease of gripping.

The inner cylinder 188 is comprised of a series of preferably three tabs each having a retaining fin 199 alternately spaced with three tabs each having a finger cam 201. The retaining fins 199 fit within openings 23 in the housing nose 29 for securing the bayonet collar to the housing. The finger cams 201 engage and raise the flexible fingers 160 of the collet 154 by engaging pins extending laterally from the upstanding tabs 161 on each finger.

Thus it will be understood that when the collar 20 is pulled rearwardly against the urging of the spring 150, the finger cams 201 pull the flexible fingers 160 of the collet 154 radially outwardly as shown in FIG. 6. However, when the collar 20 is released and permitted to move forwardly under the urging of the spring 150, the fingers 160 resiliently move radially inwardly as shown in FIG. 7 to be received in the annular groove 44, as will be described further below.

Another feature of the present invention allows the head assembly to be incrementally rotated about a longitudinal axis of the handle assembly. As shown in FIG. 10, the proximal end 17 of the head housing can be provided with a detent surface 19 complementary to the detent surface 196 on the bayonet collar 20. For example, the detent surface 19 can be shaped with radially spaced indented spherical detents for cooperating with the raised detents 198 on the bayonet collar. To rotate the head assembly 10, the bayonet collar is pulled back to the intermediate position shown in FIG. 9, and the head assembly can then be turned to the desired position. The fingers 160 of the collet will slide circumferentially in the annular groove 44 permitting 360 degree relative rotation between the head and handle assemblies. The complementary detent surfaces 196 permit indexed rotation and allow the head assembly to be releasably held in any rotational position.

The manner in which the head assembly is coupled with the handle assembly, the staple cartridge receiving jaw is pressed toward the staple deforming jaw to clamp tissue therebetween, and the staples are driven from the cartridge through the tissue to be deformed by the anvil to make a suture will now be described with reference to FIGS. 7 through 13.

Figure 7:
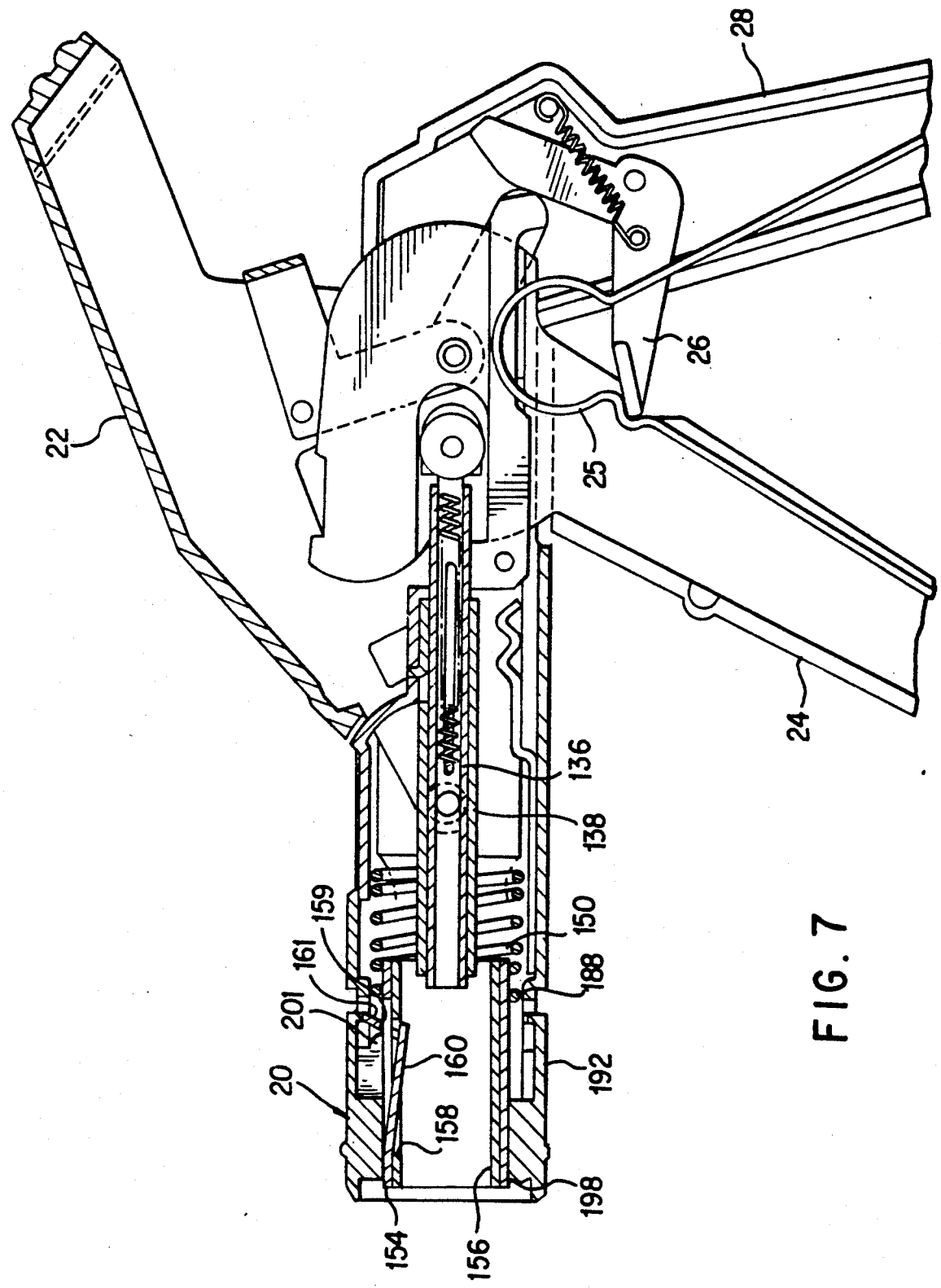
FIGS. 7 through 13 are a set of vertical cross-sectional views showing the sequence of operation of the stapling instrument in accordance with the preferred embodiment the present invention.

FIG. 7 first shows the bayonet collar 20 in its at-rest position, before it is prepared to have the head assembly attached to it. As shown there the collar spring 150 abuts the inner cylinder 188 and biases the bayonet collar 20 away from the secondary advancer 138 and secondary driver 136. In this position, the lowermost portion of the cam 201 is not in contact with the tab pins 159 of the tabs 161 and the flexible fingers 160 in their natural state are depressed through the elongated slots 158 in the nose 156 of the handle frame.

Figure 8:
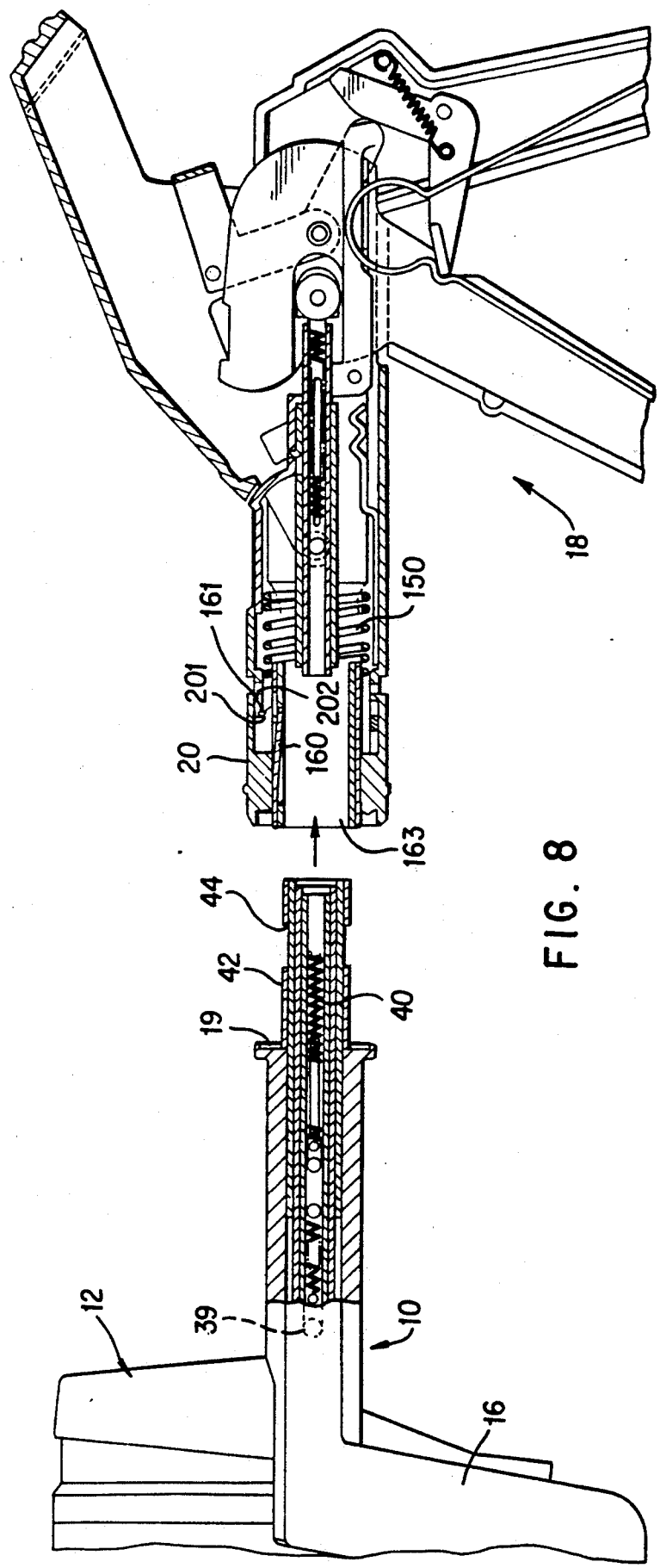

FIG. 8 shows how the handle assembly 18 is readied to receive the head assembly 10. More particularly, the bayonet collar 20, lead by interior lip 202, is pulled back against the bias of the collar spring 150 to the position shown in that Figure. At this position, the finger cams 201 engages the tab pins 159 and raise the flexible fingers 160 high enough to provide a clear passageway 163 for the head assembly 10.

Figure 9:
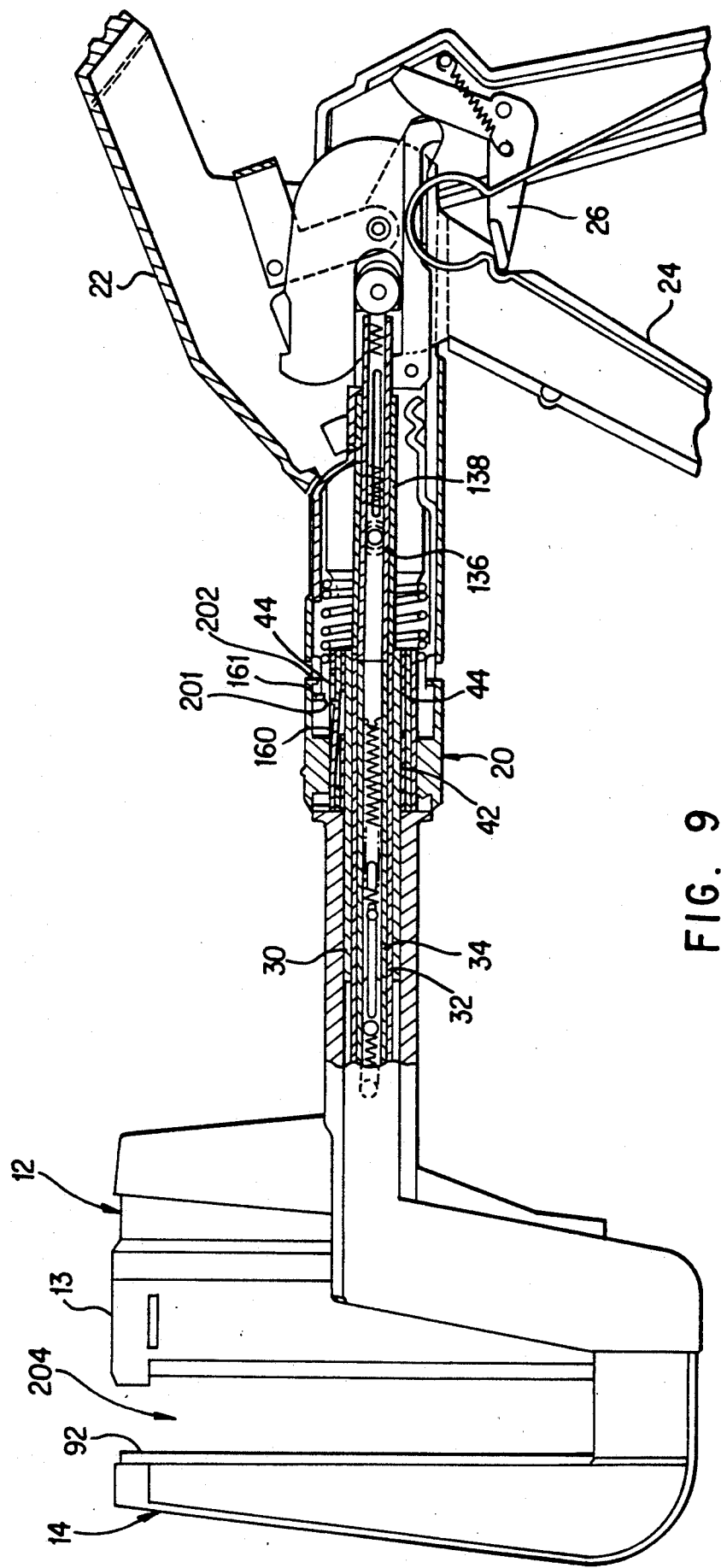
Figure 10:
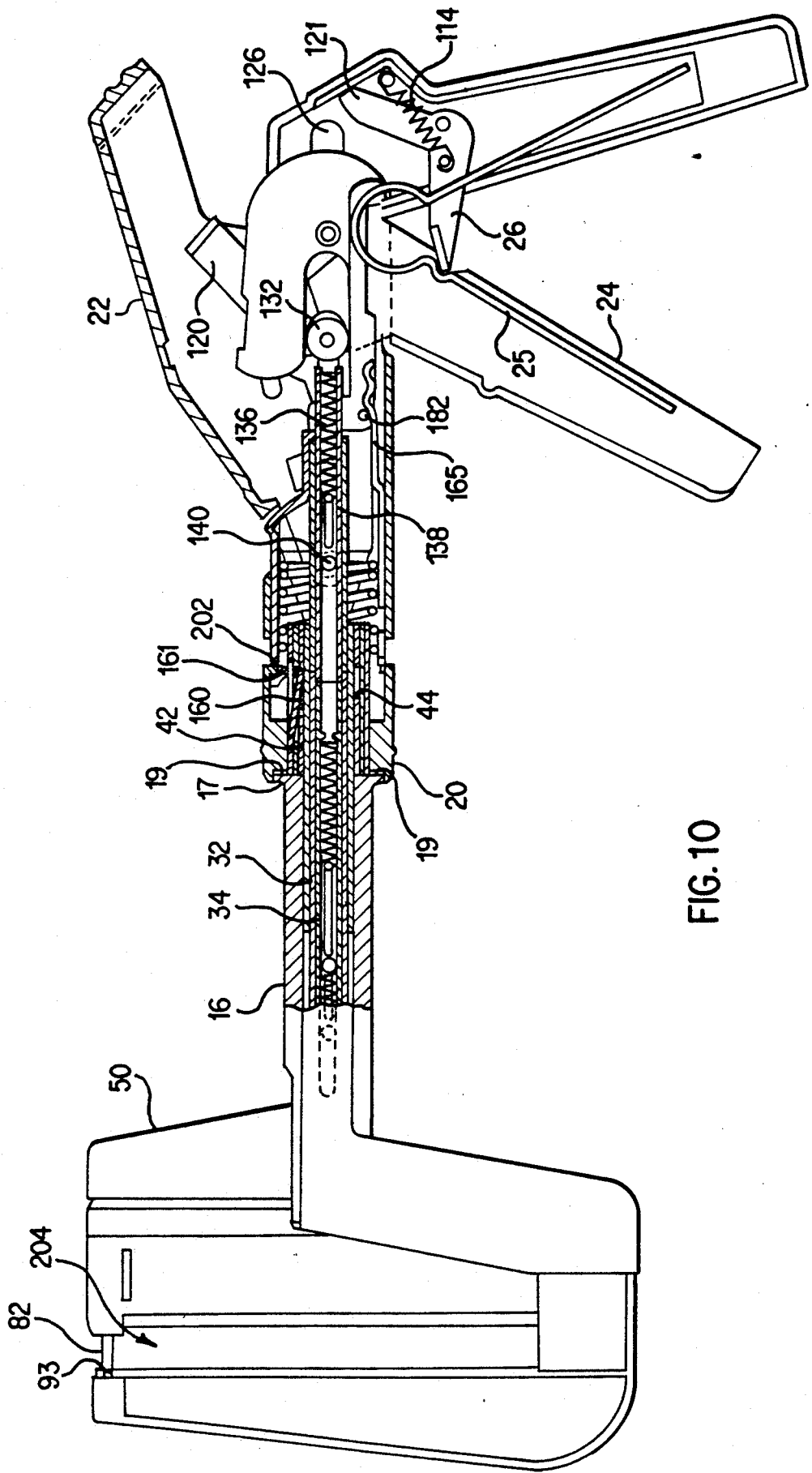

As shown in FIG. 9, while the bayonet collar 20 is held in the pulled-back position, the head assembly, led by the engagement ring 42, may be inserted into the passageway 163. When the head assembly is fully mated with the handle assembly, the annular groove 44 defined by the engagement ring 42 will align with the elongated slots 158 and flexible fingers 160. Then when the bayonet collar 20 is released as shown in FIG. 10, it springs forwardly and the finger cams 201 lower the tab pins 159, allowing the flexible fingers 160 to assume their natural biased position into the annular groove 44. In this position, the flexible fingers 160 abut the rearward surface defining the annular groove 44, and the head assembly 10 is locked into the handle assembly 18. In this coupled position, the rearward ends of the advancer 32 and driver 34 of the head assembly align with and abut the forward ends of the secondary advancer 138 and secondary driver 136, respectively, of the handle assembly.

With the head assembly 10 securely coupled to the handle assembly 18, operation of the surgical stapling instrument of the present invention can proceed through the sequence represented in FIGS. 9 through 13. In FIG. 9, the clamp lever 22 is in the fully opened position, the safety latch 26 is actuated to prevent squeezing of the trigger 24 and the loaded staple cartridge 13 is positioned in the staple cartridge receiving jaw 12. In this configuration the stapling instrument may be maneuvered to place the tissue to be sutured within a tissue gap 204 defined between the staple cartridge 13 and the anvil 92. As will be appreciated, the staple cartridge 13 is supported by the carrier track 70 of the staple cartridge receiving jaw so as to be parallel to the anvil 92. This provides a uniformly wide tissue gap 204.

With the tissue properly positioned, the clamp lever 22 is partially depressed to an intermediate position as shown in FIG. 10. This action advances the connecting pin 140, which slides the secondary advancer 138 forwardly to abut the advancer 32. The connecting pin 140 also slides the secondary driver 136 forwardly by virtue of its location at the front of the slot 142, and thus the driver 34 is advanced. The forward sliding motion of the advancer 32 overcomes the bias of the carrier spring 68 and pivots the carrier lever 50 about the pivot end 53 to advance the carrier pin 66 and aligned cartridge pin 82. At the same time, the forward sliding motion of the advancer slides the carrier track 70 forwardly in the rail slot 108 to reduce the tissue gap 204 and align the cartridge pin 82 with an alignment hole 93 in the anvil 92.

As the clamp lever 22 is initially depressed, the intermediate position is reached as the detent pin 182 in the secondary advancer engages the detent spring 165. At this position, the link 126 of the safety crank 120 remains in the path of the follower 121 of the safety latch 26 and prevents the safety latch from being disengaged.

Figure 11:
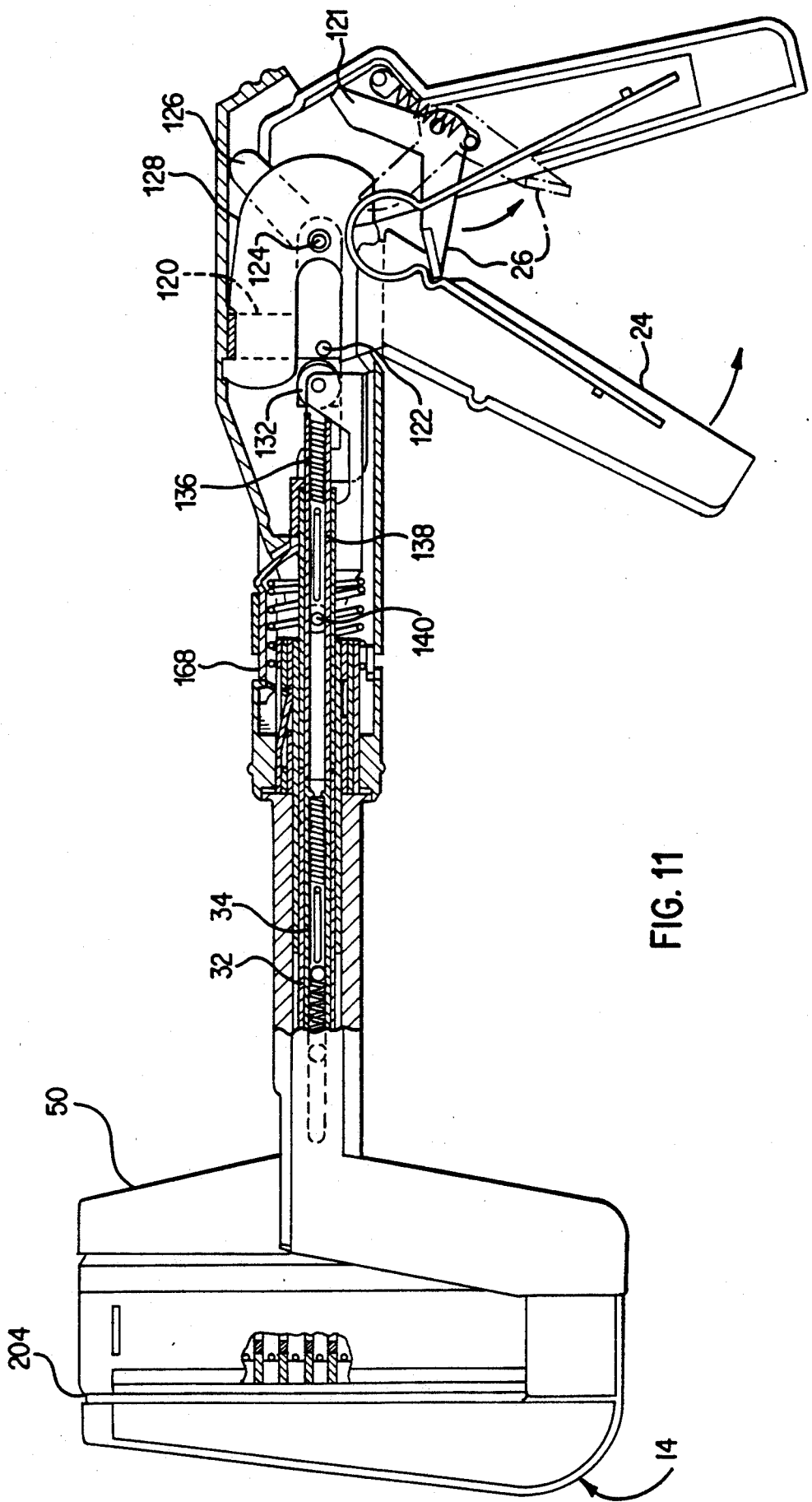
Figure 14:
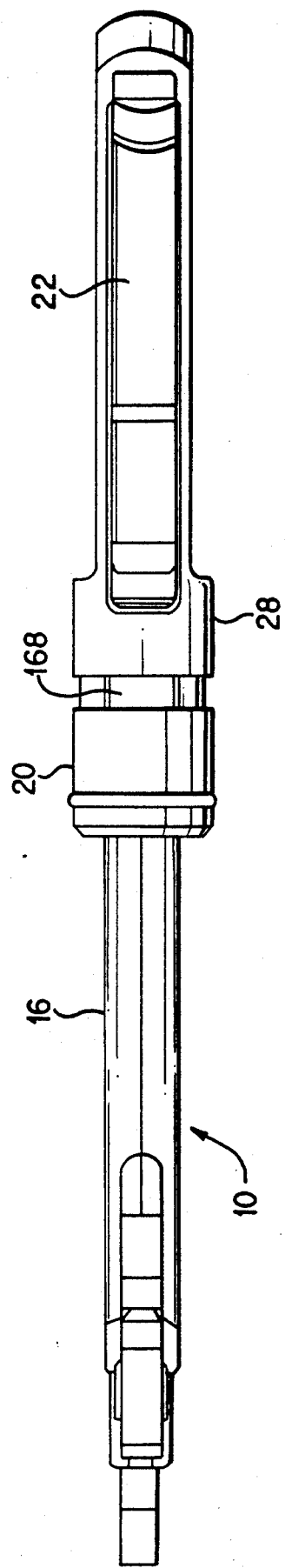
FIG. 14 is a top plan view of the surgical stapling instrument in accordance with the preferred embodiment.

The next step is to fully depress the clamp lever 22 as shown in FIG. 11. This action further advances the secondary advancer 138 and advancer 32 to close the tissue gap 204 and squeeze the tissue to be sutured. With reference again to FIG. 3, the rail slot 108 in the anvil rail 90 allows the carrier track 70 and thus the staple cartridge 13 to be advanced in a parallel sliding motion to achieve a uniform tissue closure. The closing of the clamp lever 22 also further advances the secondary driver 136 to a position where the roller bearing 132 is directly below the cam surface 130 of the trigger cam 128. The safety crank 120 is also pivoted forwardly to remove the link 126 from the path of the follower 121. In addition, the lockout indicator 168 is slid forwardly to a position where it provides a visual indicator to the operator. Indicia can be printed on the lockout indicator 168 as shown in FIG. 14 to indicate that the stapling instrument is ready to fire. The clamp lever remains closed in its fully depressed position by an over-center action of the safety crank 120. This action results from the position of the pin 122 being below a horizontal line through the rivet 24 and serves to keep the clamp lever fully depressed in the absence of any force tending to move it to its open position.

Figure 12:
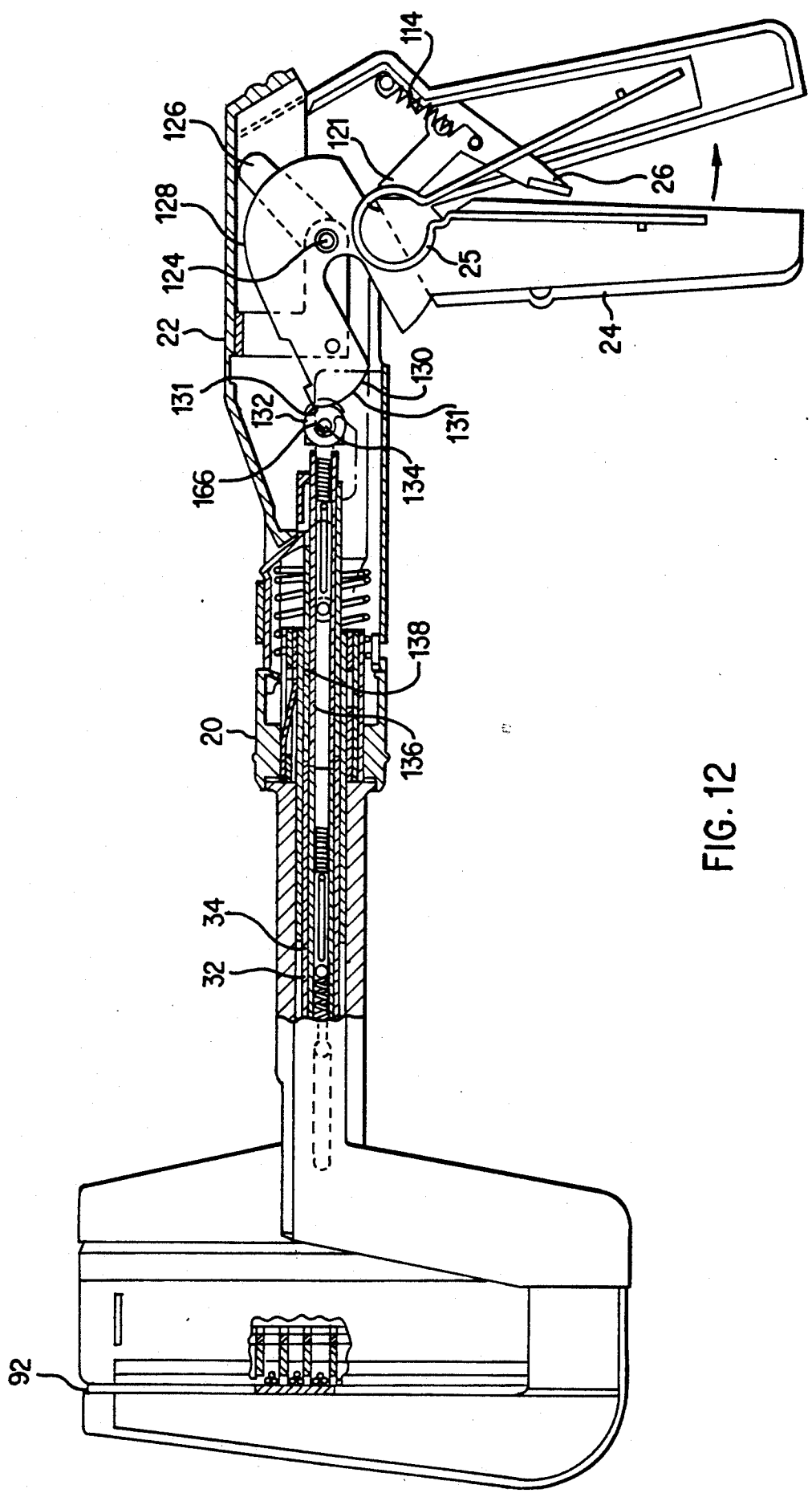

The safety latch may then be pivoted out of engagement with the trigger as depicted in FIG. 11. Accordingly, the trigger 24 may then be squeezed, or fired, as shown in FIG. 12.

Figure 3:
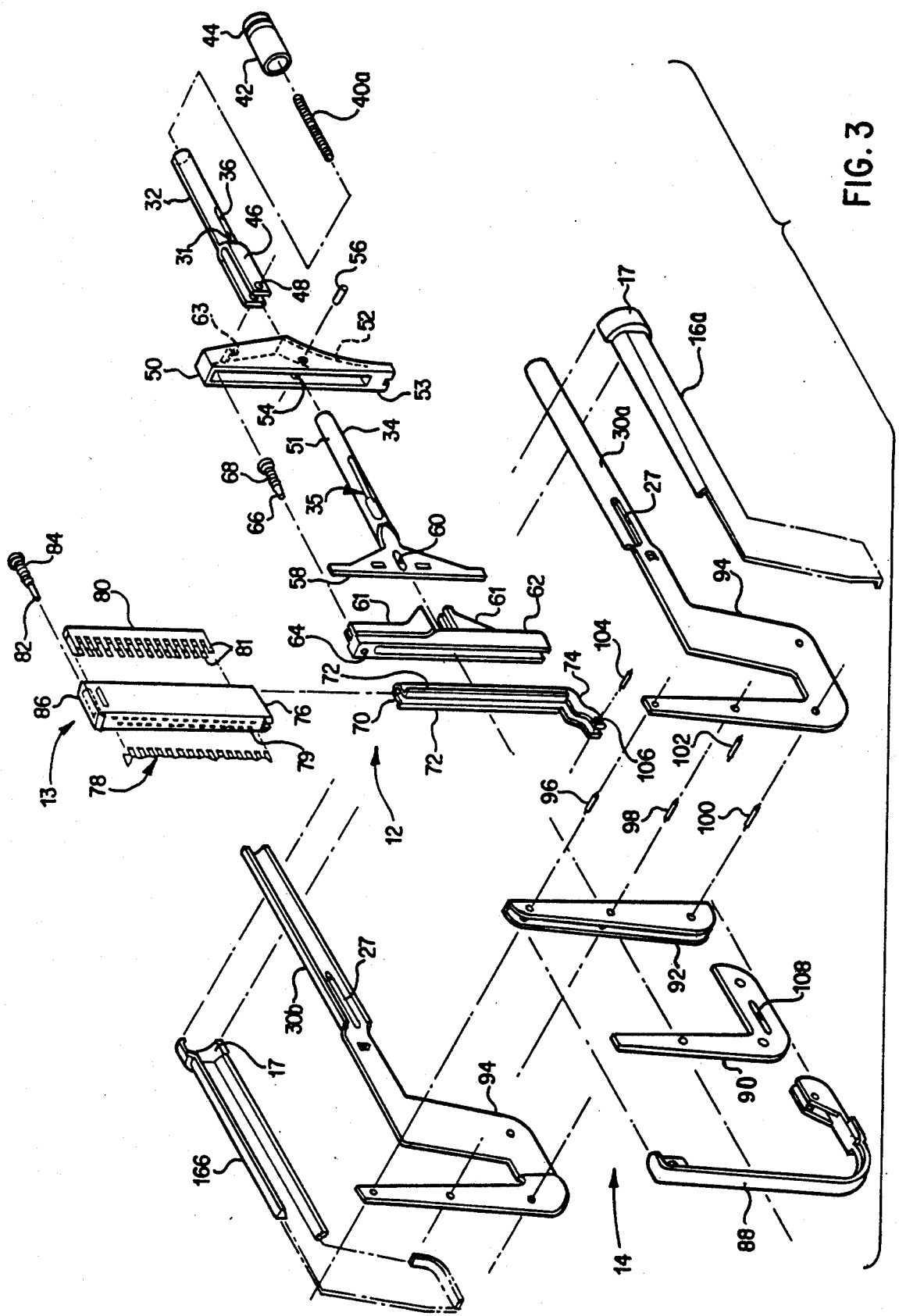
FIG. 3 is an exploded perspective view of the head assembly shown in FIG. 2.

Squeezing the trigger 24 advances the secondary driver 136 by engaging the roller bearing 132 with the cam surface 130 of the trigger cam 128. The cam surface 130 is rounded to provide tactile feedback of the stapling instrument to the operator, with the force necessary to squeeze the trigger initially increasing until an apex 131 of the cam surface passes the roller bearing 132, at which point the force decreases as the trigger squeezing is completed. When the trigger is fully squeezed and the roller bearing 132 advanced as far as possible, the bearing pin 134 of the roller bearing 132 is engaged in notch 166 in the clamp lever 22 and prevents the clamp lever 22 from being lifted. Further the fully squeezed trigger advances the secondary driver 136 and thus the driver 34 and comb 80 and in turn the staples to deform them against the anvil. In particular, as shown in FIG. 3, the advancement of the driver 34 drives the driver blade 58 against the comb 80 to force the staples 78 through the tissue and against the anvil 92 to be deformed. Additionally, since the clamp lever is held in the closed position by the engagement of the bearing pin with the notch 166 in the clamp lever, the staple cartridge and anvil cannot be prematurely separated.

Figure 13:
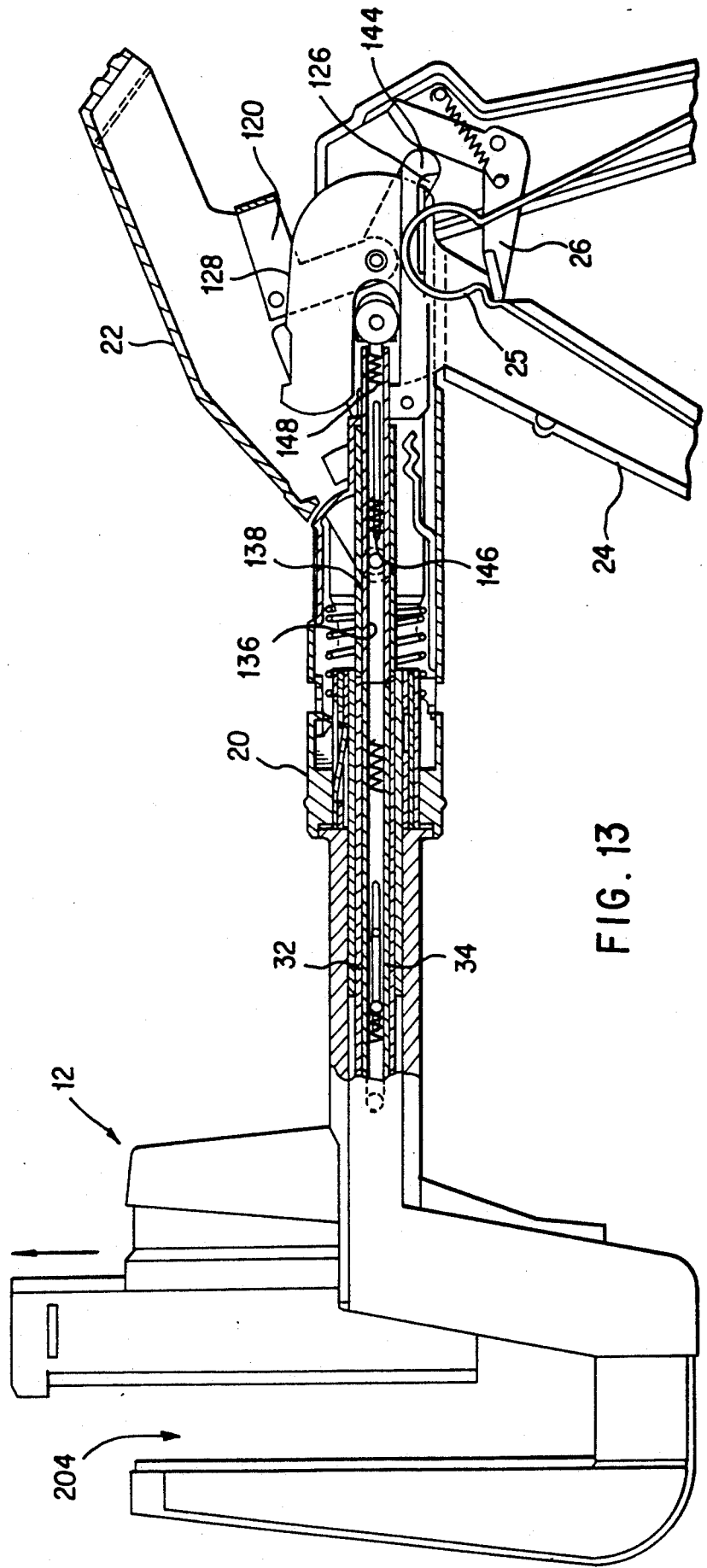

When the trigger 24 is released, the clamp lever 22 can again be lifted as shown in FIG. 13. Lifting the lever pulls the secondary advancer 138 rearwardly to its rest position, and the secondary driver is retracted by the biasing action of the driver spring 148 on the fixed pin 146. The rearward movement of the secondary advancer causes its stepped extension 144 to rotate the safety latch 26 and return it to the engaged position. In addition, the lifting of the clamp lever 22 positions the crank 126 of the safety link 120 against the follower 121 of the safety latch 26 again to lock it in the engaged position.

As noted, in the head assembly 10, the driver spring 40a is compressed between the fixed pin 38 and the nubs 37 in the driver 34 to bias the advancer 32 and driver 34 rearwardly. Rearward movement of the advancer 32 also retracts the staple cartridge receiving jaw 12, as the pin 104 slides rearwardly in the rail slot 108 of the anvil rail 92 to open up the tissue gap 204. The spent cartridge 15 can be replaced with a loaded cartridge and the stapling instrument is ready for another stapling operation.

Those skilled in the art will understand from the detailed description provided above that the present invention provides many substantial improvements on known surgical stapling instruments and particularly known transverse anastomosis stapling instruments. These include the following:

The trigger for causing staple deformation is provided with a secure safety latch which is only disengaged when the instrument is properly prepared to form a suture. At all other times, when the staple cartridge receiving jaw and stapling deforming jaw are withdrawn from one another, the safety latch is automatically engaged.

The instrument accommodates different staple cartridges having different comb and complementary staple lengths so that different staples used in different suturing applications can be used by the same instrument.

The clamp lever and associated staple cartridge advancing mechanism are designed to advance the cartridge toward the anvil with a short forward and downward motion that is easily performed by a surgeon's thumb.

Further, the staple cartridge supporting elements permit it to move toward the anvil in parallel to it. Thus, uniform tissue clamping pressure can be achieved.

The head assembly is fully removable from the handle assembly. Therefore, even if the instrument of the invention is designed to be disposable, it is possible to reuse the handle assembly which generally remains remote from the suturing site. The head assembly is also rotatable relative to the handle assembly about the longitudinal axis of each. Accordingly, the head assembly can be placed in any rotational position desired by the surgeon that makes the handle assembly most easy to use.

The trigger cam and cam follower for driving and deforming staples are designed to give the surgeon tactile feedback when the staples have been fully deformed and closure is complete.

The clamp lever is also prevented from being opened while the trigger is squeezed. Therefore the jaws cannot be opened while the staple drivers are in an advanced position.

Although a specific embodiment of the present invention has been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What we claim is:

1. A surgical stapling instrument, comprising:
   (a) a head assembly including;
      (1) a staple cartridge that may be loaded with surgical staples;
      (2) an anvil mounted to confront said staple cartridge for deforming staples driven theretoward;
      (3) primary advancing means operable to advance said staple cartridge from an open position toward said anvil to a closed position for clamping tissue to be sutured therebetween;
      (4) primary driving means operable to drive staples from said cartridge through tissue toward said anvil to deform the staples; and
      (5) a head housing, at least a portion of said primary advancing means being mounted in said head housing for reciprocal movement in the direction of a first longitudinal axis and at least a portion of said primary driving means also being mounted in said head housing for reciprocal movement in the direction of the first longitudinal axis;
   (b) a handle assembly including;
      (1) secondary advancing means couplable with said primary advancing means to operate said primary advancing means to advance said staple cartridge to the closed position;
      (2) secondary driving means couplable with said primary driving means to operate said primary driving means to deform the staples; and
      (3) a handle housing, at least a portion of said secondary advancing means being mounted in said handle housing for reciprocal movement in the direction of a second longitudinal axis, and at least a portion of said secondary driving means also being mounted in said handle housing for reciprocal movement in the direction of the second longitudinal axis; and
   (c) means for removably mounting said handle assembly and said head assembly together with said secondary advancing means coupled to said primary advancing means and with said secondary driving means coupled to said primary driving means, with said primary advancing means and said secondary advancing means abutting each other in coaxial alignment to transmit axial force therebetween, and with said primary driving means and said secondary driving means abutting each other in coaxial alignment to transmit axial force therebetween.

2. The surgical stapling instrument according to claim 1, wherein said mounting means comprises a collar secured on one of said handle assembly and said head assembly, and a sleeve secured on the other of said handle assembly and said head assembly; said collar being formed to removably receive said sleeve in telescoping fashion.

3. The surgical stapling instrument according to claim 2, wherein said mounting means further comprises means for releasably locking said collar and said sleeve together.

4. The surgical stapling instrument according to claim 1, wherein said mounting means mounts said handle assembly and said head assembly together along a longitudinal axis and further comprises means for permitting said head assembly to rotate relative to said handle assembly about the longitudinal axis.

5. The surgical stapling instrument according to claim 4, wherein said cartridge and said anvil extend in a direction not parallel to the longitudinal axis.

6. The surgical stapling instrument according to claim 4, wherein said cartridge and said anvil extend generally perpendicularly to the longitudinal axis.

7. The surgical stapling instrument according to claim 4, further comprising means for preventing rotation of said head assembly relative to said handle assembly through said permitting means when said cartridge is advanced to the closed position by said coupled primary and secondary advancing means.

8. The surgical stapling instrument according to claim 1, further comprising means for preventing said mounting means from being operated to demount said handle assembly and said head assembly when said cartridge is advanced to the closed position by said coupled primary and secondary advancing means.

9. A surgical stapling instrument, comprising:
   (a) a head assembly including;
      (1) a staple cartridge that may be loaded with surgical staples;
      (2) an anvil mounted to confront said staple cartridge for deforming staples driven theretoward;
      (3) primary advancing means mounted for axial reciprocal movement in the direction of a longitudinal axial and operable to advance said staple cartridge from an open position toward said anvil to a closed position for clamping tissue to be sutured therebetween;
      (4) primary driving means mounted for axial reciprocal movement in the direction of the longitudinal axis and operable to drive staples from said cartridge through tissue toward said anvil to deform the staples;
   (b) a handle assembly including;
      (1) secondary advancing means couplable with said primary advancing means to operate said primary advancing means to advance said staple cartridge to the closed position; and
      (2) secondary driving means couplable with said primary driving means to operate said primary driving means to deform the staples; and
   (c) means for mounting said handle assembly and said head assembly together along the longitudinal axis, said mounting means including means permitting said head assembly to rotate relative to said handle assembly about the longitudinal axis, with said primary advancing means and said secondary advancing means abutting each other in coaxial alignment to transmit axial force therebetween, and with said primary driving means and said secondary driving means abutting each other in coaxial alignment to transmit axial force therebetween.

10. The surgical stapling instrument according to claim 9,
    wherein said head assembly includes a head housing, at least a portion of said primary advancing means being mounted in said head housing for reciprocal movement in the direction of a first longitudinal axis and at least a portion of said primary driving means also being mounted in said head housing for reciprocal movement in the direction of the first longitudinal axis;

wherein said handle assembly includes a handle housing, at least a portion of said secondary advancing means being mounted in said handle housing for reciprocal movement in the direction of a second longitudinal axis, and at least a portion of said secondary driving means also being mounted in said handle housing for reciprocal movement in the direction of the second longitudinal axis; and wherein said mounting means is arranged to mount said handle assembly and said head assembly together with said first and second longitudinal axes coincident with said portion of said primary and secondary advancing means abutting each other in coaxial alignment to transmit axial force therebetween and with said portion of said primary and secondary driving means abutting each other in coaxial alignment to transmit axial force therebetween.

11. The surgical stapling instrument according to claim 9, wherein said mounting means comprises a collar secured on one of said handle assembly and said head assembly, and a sleeve secured on the other of said handle assembly and said head assembly, said collars being formed to removably receive said sleeve in telescoping fashion.

12. The surgical stapling instrument according to claim 9, wherein said cartridge and said anvil extend in a direction not parallel to the longitudinal axis.

13. The surgical stapling instrument according to claim 9, wherein said cartridge and said anvil extend generally perpendicularly to the longitudinal axis.

14. The surgical stapling instrument according to claim 9, further comprising means for preventing rotation of said head assembly relative to said handle assembly through said permitting means when said cartridge is advanced to the closed position by said coupled primary and said secondary advancing means.

15. The surgical stapling instrument according to claim 9, wherein said mounting means removably mounts said head assembly and said handle assembly together.

16. A surgical stapling instrument, comprising:
(a) a staple cartridge that may be loaded with surgical staples;
(b) an anvil configured to confront said staple cartridge for deforming staples driven theretoward;
(c) means for mounting said staple cartridge for reciprocal movement toward and away from said anvil in mutually parallel relation;
(d) advancing means for advancing said staple cartridge on said mounting means from an open position toward said anvil to a closed position for clamping tissue to be sutured therebetween;
(e) driving means for driving the staples from said cartridge toward said anvil through tissue clamped between said cartridge and said anvil;
(f) clamping means for operating said advancing means; and
(g) trigger means for operating said driving means, wherein
said advancing means includes a primary advancer and a secondary advancer abutting each other in coaxial alignment to transmit axial force therebetween; wherein said clamping means is coupled to said secondary advancer to reciprocate said secondary advancer in a direction of a first longitudinal axis to transmit an axial force to said primary advancer; wherein said driving means includes a primary driver and a secondary driver abutting each other in coaxial alignment to transmit axial force therebetween; and wherein said trigger means is coupled to said secondary driver to reciprocate in a direction of the first longitudinal axis to transmit an axial force to said primary driver.

* * * * *